United States Patent [19]
Davey et al.

[11] Patent Number: 5,821,375
[45] Date of Patent: Oct. 13, 1998

[54] PREPARATION OF NORLABDANE OXIDE

[75] Inventors: Paul Nicholas Davey; Laurence Sidney Payne, both of Kent, Great Britain; Chi-lam Tse, Shatin N T, Hong Kong

[73] Assignee: Quest International B.V., Naarden, Netherlands

[21] Appl. No.: 905,116

[22] Filed: Aug. 1, 1997

[30] Foreign Application Priority Data

Aug. 2, 1996 [EP] European Pat. Off. ............... 96305708

[51] Int. Cl.⁶ .................................................. C07D 307/92
[52] U.S. Cl. ............................................................ 549/458
[58] Field of Search ............................................. 549/458

[56] References Cited

U.S. PATENT DOCUMENTS

| | | | |
|---|---|---|---|
| 3,050,532 | 8/1962 | Schumacher et al. | 260/343.3 |
| 5,463,089 | 10/1995 | Barton et al. | 549/458 |
| 5,473,085 | 12/1995 | Barton et al. | 549/458 |

FOREIGN PATENT DOCUMENTS

| | | | |
|---|---|---|---|
| 0 296 564 | 12/1988 | European Pat. Off. | C07D 307/92 |
| 0 752 423 A1 | 1/1997 | European Pat. Off. | C07D 307/92 |
| 39 42 358 A1 | 6/1991 | Germany | C07D 307/92 |
| 41 23 767 A1 | 1/1993 | Germany | C07D 307/42 |
| 44 39 574 A1 | 5/1996 | Germany | C07D 307/92 |

*Primary Examiner*—Bernard Dentz
*Attorney, Agent, or Firm*—Pillsbury Madison & Sutro, LLP

[57] ABSTRACT

The invention concerns a process for preparing (−)-norlabdane oxide from sclareol oxide comprising the steps of:

I converting sclareol oxide to 12-acetylnorlabdane oxide by oxidation with an organic hydroperoxide;

II converting 12-acetylnorlabdane oxide to 12-acetoxy-norlabdane oxide by oxidation with an organic peracid.

Step I is preferably performed with tert-butyl hydroperoxide and step II with peracetic acid.

Sclareol oxide may be prepared from sclareol by ozonolysis followed by treatment with alkaline hydrogen peroxide. 12-Acetoxy-norlabdane oxide is preferably converted to norlabdane oxide by reduction with $NaBH_4$ in the presence of a transition metal salt.

14 Claims, No Drawings

PREPARATION OF NORLABDANE OXIDE

The present invention relates to the synthesis of the fragrance material 1,2,3a,4,5,5a,6,7,8,9,9a,9b-dodecahydro-3a,6,6,9a-tetramethylnaphto-(2,1-b)-furan, also known as (−)-norlabdane oxide.

(−)-Norlabdane oxide, of formula (1) below, is a well known fragrance material. It is the most widely used material for providing an ambergris-type odour to perfumes and is sold under various trade names, notably as Amberlyn, Ambroxan, Ambrox or Amberoxide. A number of synthetic procedures for this compound have been published. Many use naturally occurring (−)-sclareol of formula (2) below as the starting material from which the norlabdane oxide is obtained in a multistep synthesis. All processes starting from sclareol have in common that they proceed via the diol of formula (3) below as an intermediate, which has to be cyclized to give compound (1). This cyclization requires considerable care to prevent the formation of the more thermodynamically stable iso-form of (1), which has inferior olfactive properties, and the elimination of the tertiary alcohol group.

Recently U.S. Pat. Nos. 5,463,089 and 5,473,085 were published which describe the conversion of sclareol to 12-acetyl-norlabdane oxide, of formula (4) below by oxidation/rearrangement with $OsO_4/NaIO_4$, followed by Baeyer-Villiger oxidation with m-chloroperbenzoic acid in sodium acetate buffer to 12-acetoxy-norlabdane oxide, of formula (5) below. This acetate was thereafter reduced to (1) with $LiAlH_4/BF_3.OEt_2$. These US patents also provide a list of literature references describing the various procedures published for converting sclareol to norlabdane oxide.

Also various procedures are known to oxidize sclareol to sclareolide, as a first step in the final synthesis of norlabdane oxide. Chromium trioxide (SU-A-345,153), potassium permanganate (JP-A-61 033184), ruthenium tetroxide (DE-A-3942358) have all been used as well as microbial oxidation (U.S. Pat. Nos. 4,798,799 and 4,970,163). In SU-A-1,409, 631 a two step oxidation with ozone at low temperature, followed by treatment with alkali at high temperature, is described.

Less is known about the conversion of sclareol into sclareol oxide, of formula (6) below. L. Ruzicka et al, Helv. Chim Acta 25 (1942), 621 and D. B. Bigley et al, J. Chem. Soc. 1960 4613 describe the oxidation with $KMnO_4$. However, no yield was reported. B. Waegell et al, Tetrahedron Letters 1994 (35), 497 describe the conversion by Ru-catalysed oxidation but again no yield was reported In U.S. Pat. No. 5,247,100 (equivalent to DE-A-3942358 vide supra) the conversion to sclareolide proceeds via sclareol oxide. P. F. Vlad, Khim. Prir. Soedin., 1991, (1) 43 and (4) 502 obtained sclareol oxide via ozonolysis as a mixture with other components and in a maximum yield of 54%.

Although the procedure to obtain norlabdane oxide as described in U.S. Pat. Nos. 5,463,089 and 5,473,085 mentioned above provide a simplified procedure compared to those published previously, they are not well suited to use on an industrial scale. Osmium tetroxide is a very toxic chemical and therefore not suitable for large scale use. M-chloroperbenzoic acid is expensive and objectionable from an environmental point of view. Therefore, there is a need for a process to convert sclareol to norlabdane oxide in high yield, using simple, environmentally friendly and low toxicity chemicals. It is therefore an object of the present invention to provide a process for the preparation of norlabdane oxide from sclareol comprising improved process steps.

A process has now been found to produce (−)-norlabdane oxide from sclareol oxide which comprises the steps of:
  I converting sclareol oxide to 12-acetylnorlabdane oxide by oxidation with an organic hydroperoxide;
  II converting 12-acetylnorlabdane oxide to 12-acetoxynorlabdane oxide by oxidation with an organic peracid.

The organic hydroperoxide used in step I is preferably a hydroperoxide derived from an aliphatic or alicyclic alcohol, particularly a tertiary alcohol. Tert-butyl hydroperoxide is very suitable. These hydroperoxides may be prepared in situ by using the corresponding alcohol as solvent or cosolvent for sclareol oxide and adding hydrogen peroxide to the solution. The reaction is preferably carried out in the presence of a catalytic amount of iodine. The reaction temperature may be chosen between 0° and 50° C., preferably between 10° and 30° C. After the reaction any excess peroxide may be removed according to usual procedures by treatment with a suitable reducing agent, such as a thiosulphate salt. The 12-acetyl-norlabdane oxide is obtained in high yield as a mixture of 12-epimers which can be used in step II without any further purification or separation.

The sclareol oxide used as the starting material in step I may be obtained by any of the methods described in the art. A preferred, novel and improved method involves the oxidation of sclareol with ozone, followed by treatment with alkaline hydrogen peroxide. This ozonolysis can be performed under usual ozonolysis conditions, using a temperature of −20°−+40° C., preferably +10°−+30° C., more preferably and for the sake of convenience at around room temperature (15°−25° C.). A solvent may be used which is usual for ozonolysis reactions such as a lower alcohol, a lower aliphatic acetate or methylene chloride, preferably a C1–C5 alcohol such as methanol or ethanol.

The hydrogen peroxide oxidation can be performed with dilute hydrogen peroxide, particularly 1–30% in water, in the presence of a suitable base, such as an alkaline or alkaline earth metal hydroxide, particularly NaOH or KOH. After the reaction any excess peroxide may be removed according to usual procedures by treatment with a suitable reducing agent, such as a thiosulphate salt. Sclareol oxide is obtained in high yield and can be used in step I without further purification.

The reaction with the organic peracid (step II) is carried out in a solvent which is inert to the reagent. Aliphatic or alicyclic ethers are particularly suitable, such as tert-butyl methyl ether. Although various organic peracids are suitable for the reaction, a lower (e.g. C1–C5) aliphatic peracid is preferred. Peracetic acid is particularly suitable. As usual in Baeyer-Villiger oxidations, an anhydrous buffer salt should be present, such as sodium acetate, or preferably sodium formate. The reaction can be carried out between 0° and 30° C., preferably, and for the sake of convenience at around room temperature (15°−25° C.). After the reaction any excess peracid may be removed according to usual procedures by treatment with a suitable reducing agent, such as a thiosulphate salt. The 12-acetoxy-norlabdane oxide is obtained in high yield and again as a mixture of epimers.

Step I and II may be carried out succesively without purification of the product of step I. They may even be carried out in one pot without isolation of the acetylnorlabdane oxide. This also holds for the ozone oxidation of sclareol to sclareol oxide and step I. Even the total reaction sequence from sclareol to 12-acetoxy-norlabdane oxide may be carried out without purification of the intermediates, and even in one pot without isolation of the intermediates.

The 12-acetoxy-norlabdane oxide can be converted to (−)-norlabdane oxide by complex metal hydride reduction, particularly with LiAlH$_4$/BF$_3$-etherate as described in U.S. Pat. Nos. 5,463,089 and 5,473,085.

A novel and very convenient process uses NaBH$_4$ in the presence a transition metal salt, particularly a transition metal halogenide such as ZnCl$_2$, FeCl$_3$, or CuBr. Sometimes this gives rise to a mixture of norlabdane oxide and diol (3). After separation of the mixture, the diol may be cyclized as described in the prior art.

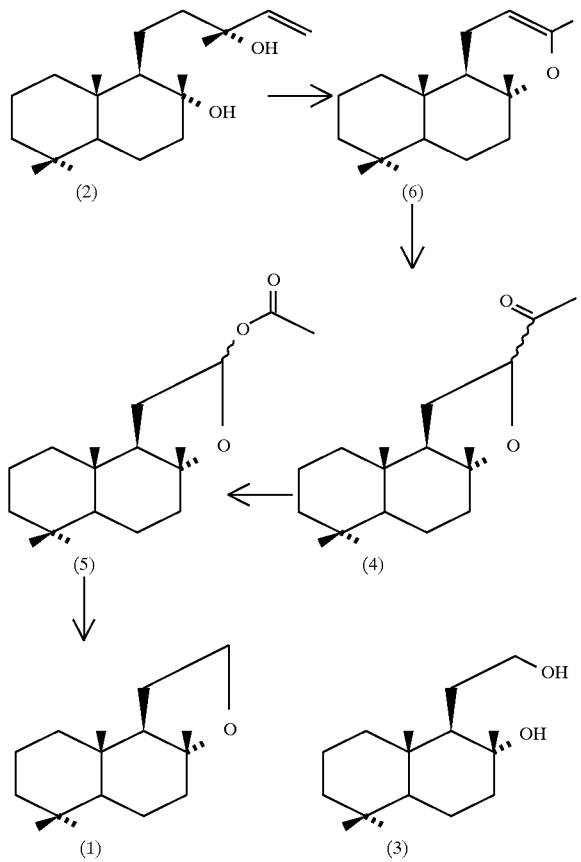

The invention is further illustrated by the following non-limiting examples:

Preparation of sclareol oxide 40.6 g of sclareol (0.132 mol) in 300 ml methanol was ozonolysed at 20°–25° C. using a Gebr. Herrmann LAB-50-1 lab ozoniser operating at 130V, with flow rate at 6 l/hr, under which conditions 0.05 mol/hr of ozone was generated. The reaction was complete in 3 hrs whereafter the reaction mixture was poured into a mixture of 19 g KOH and 38 ml H$_2$O$_2$ in 500 ml of water and stirred for 30 min. The suspension was extracted three times with 100 ml toluene. the organic layer was washed with 100 ml 0.1 mol sodium thiosulphate solution and dried over Mg sulphate. Thereafter toluene was removed at 55° C. under reduced pressure. 33.6 g (97.4% yield) of pure sclareol oxide was obtained.

Preparation of 12-acetyl-norlabdane oxide

To a solution of 5.5 g (21 mmol) of sclareol oxide obtained above in 10 ml tert-butanol was added 5 ml of a 30% aqueous hydrogen peroxide solution (44.1 mmol H$_2$O$_2$) and the solution was stirred for 10 min while a white emulsion formed. To this 0.34 g (1.33 mmol) of iodine was added and the mixture was stirred at room temperature for 2 hours during which it turned to orange brown due to slow dissolution of the iodine. Then the solution was warmed up to 75° C. and the colour changed to deep brown, whereafter it was cooled down slowly. The reaction was shown to be completed in 2 hours by TLC and NMR. Then 25 ml of saturated sodium thiosulphate was added to the reaction mixture and stirred for 30 min, during which the solution became colourless. The reaction mixture was extracted three times with 10 ml tert-butyl methyl ether. The combined organic layers were washed with another 20 ml of saturated sodium thiosulphate solution and dried over Mg sulphate. The solvent was evaporated and 12-acetyl-norlabdane oxide was obtained in 92% yield as a 1:5 mixture of both 12-epimers.

Preparation of 12-acetoxy-norlabdane oxide

To a solution of 0.63 g (2.25 mmol) of the epimer mixture of 12-acetyl-norlabdane oxide obtained above in 30 ml tert-butyl methyl ether was added 0.408 g (6 mmol) of anhydrous sodium formate and the mixture stirred for 30 min. to obtain a homogeneous suspension. 0.6 ml of a 35.5% aqueous peracetic acid solution (2.8 mmol) was added and the suspension stirred at 25°–30° C. for 20 hours. Thereafter 30 ml of saturated sodium thiosulphate solution was added and the mixture stirred for 20 minutes. The organic layer was separated and the aqueous layer extracted twice with 30 ml tert-butyl methyl ether. The combined organic layers were washed again with saturated sodium thiosulphate solution and twice with saturated sodium bicarbonate solution. The organic layer was dried over Mg sulphate and the solvent evaporated to afford 0.618 g of crude 12-acetoxy-norlabdane oxide. This was purified by column chromatography using hexane and diethyl ether as eluents. 0.606 g (91.5%) of the pure product was obtained as a 1:5 epimeric mixture.

Preparation of norlabdane oxide

Process A

To a solution of 0.532 g (1.81 mmol) of the epimeric acetate mixture obtained above in 10 ml diglyme 0.147 g (3.88 mmol) sodium borohydride and 0.15 g (1.1 mmol) of zinc chloride were added while stirring. The mixture was warmed slowly to 80° C. and stirred at that temperature for 4 hours. The reaction was shown to be completed by NMR and the reaction mixture was cooled down to room temperature. Then 2 ml of acetone were added to the reaction mixture and stirred for 30 minutes, whereafter the reaction mixture was poured into 20 ml saturated sodium bicarbonate solution. The mixture was extracted three times with 20 ml cyclohexane. The combined organic layers were washed with brine and dried over magnesium sulphate whereafter the solvent was evaporated. The crude product obtained was separated using column chromatography with hexane and diethyl ether as the eluents. 0.174 g (40.8%) of norlabdane oxide was obtained and 0.251 (54%) of the diol (6).

Process B

To a solution of the epimeric acetate mixture (5) (7.22 g, 0.0246 mol) in 70 ml THF, sodium borohydride (1.797 g, 0.0475 mol) was added, the solution was warmed up and gas evolved as the hydride was added. The suspension was stirred for ten minutes and it was cooled down with an ice bath. The anhydrous ferric chloride (3.373 g, 0.02 mol) was added very slowly, gas evolved and the suspension turned black. The suspension turned rusty brown in 5 hours and according to TLC, the reaction was completed. The reaction mixture was then poured slowly with cooling into 20 ml acetone and stirred for 20 minutes. The mixture was poured into 50 ml brine and 50 ml cyclohexane was added. The organic layer was separated and the aqueous layer was washed with more cyclohexane (2×50 ml). The combined organic layer was dried, filtered and the solvent was stripped. 5.336 g crude product was isolated. From quantitative GC analysis the yield of norlabdane oxide was 82% and of the diol 5%.

Process C

To a solution of the epimeric acetate mixture (5) (12.02 g, 0.041 mol) in 50 ml THF, cooled in an ice bath, sodium borohydride (2.99 g, 0.081 mol) was added slowly in portions. The solution warmed up and gas evolved as the hydride was added. The suspension was stirred for 10 minutes. Copper(I) Bromide (5.86 g, 0.041 mol) was added very slowly, gas evolved and the suspension turned black. The reaction mixture was slowly warmed to room temperature and stirred for 1 day. The mixture was then poured slowly and with stirring into 50 ml brine cooled in an ice bath. Celite (3 g) was added and stirred until no more gas evolved, whereafter the mixture was filtered. The filtered black solid was washed four times with 50 ml cyclohexane. The combined organic layers were washed twice with 50 ml saturated ammonium chloride solution and once with brine (50 ml). Thereafter it was dried. The solvent was evaporated and 8.99 g crude product was obtained. According to quantitative GC analysis 86.6% yield of norlabdane oxide was obtained

We claim:

1. Process for preparing (−)-norlabdane oxide from sclareol oxide which comprises the steps of:
   I. converting sclareol oxide to 12-acetylnorlabdane oxide by oxidation with an organic hydroperoxide;
   II. converting 12-acetylnorlabdane oxide to 12-acetoxy-norlabdane oxide by oxidation with an organic peracid; and
   III. reducing the 12-acetoxy-norlabdane oxide to (−)-norlabdane oxide.

2. Process according to claim 1 wherein the hydroperoxide is derived from an aliphatic or alicyclic alcohol.

3. Process according to claim 2, wherein the hydroperoxide is derived from a tertiary alcohol.

4. Process according to claim 3 wherein the tertiary hydroperoxide is tert-butyl hydroperoxide.

5. Process according to claim 2 wherein the hydroperoxide is prepared in situ from the corresponding alcohol and hydrogen peroxide.

6. Process according to claim 1 wherein the organic peracid is an aliphatic C1–C5 peracid.

7. Process according to claim 6 wherein the organic peracid is peracetic acid.

8. Process according to claim 1 wherein the sclareol oxide is prepared by ozonolysis of sclareol followed by treatment with alkaline hydrogen peroxide.

9. Process according to claim 8 wherein the ozonolysis of sclareol and step I are carried out in one pot without isolation of the sclareol oxide.

10. Process according to claim 7 wherein the oxidation with peracetic acid is carried out in the presence of sodium formate.

11. Process according to claim 1 wherein steps I and II are carried out in one pot without isolation of the 12-acetyl-norlabdane oxide.

12. Process for preparing (−)-norlabdane oxide wherein 12-acetoxy-norlabdane oxide is converted to norlabdane oxide by reduction with $NaBH_4$ in the presence of a transition metal salt.

13. Process according to claim 12 wherein the transition metal salt is a halogenide.

14. Process according to claim 13 wherein the transition metal halogenide is chosen from $ZnCl_2$, $FeCl_3$ or CuBr.

* * * * *